(12) United States Patent
Boyd et al.

(10) Patent No.: US 6,468,311 B2
(45) Date of Patent: Oct. 22, 2002

(54) MODULAR INTERBODY FUSION IMPLANT

(75) Inventors: Lawrence M. Boyd, Durham, NC (US); Eddie F. Ray, III, Cordova, TN (US); Jeffrey Kozak, Houston, TX (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/766,948

(22) Filed: Jan. 22, 2001

(65) Prior Publication Data

US 2002/0099444 A1 Jul. 25, 2002

(51) Int. Cl.⁷ ................................................ A61F 2/44
(52) U.S. Cl. .................................. 623/17.16; 623/17.11
(58) Field of Search ............................ 623/17.11, 17.16

(56) References Cited

U.S. PATENT DOCUMENTS

| | | | |
|---|---|---|---|
| 5,397,364 A | 3/1995 | Kozak et al. ................. | 623/17 |
| 5,989,289 A | 11/1999 | Coates et al. ................. | 623/17 |
| 6,033,438 A | * 3/2000 | Bianchi et al. ............... | 623/17 |
| 6,174,311 B1 | 1/2001 | Branch et al. ................ | 606/61 |
| 6,224,631 B1 | * 5/2001 | Kohrs ..................... | 623/17.11 |
| 6,258,125 B1 | * 7/2001 | Paul et al. ............... | 623/17.11 |

OTHER PUBLICATIONS

U.S. patent application Ser. No. 09/369,975, McKay, filed Aug. 6, 1999.

* cited by examiner

*Primary Examiner*—David H. Willse
*Assistant Examiner*—Thomas Barrett
(74) *Attorney, Agent, or Firm*—Woodard, Emhardt, Naughton, Moriarty & McNett (57) ABSTRACT

An interbody fusion device for engagement between vertebrae includes a pair of lateral spacers for spacing the vertebrae, and a connecting member adapted to couple together the lateral spacers when inserted between the vertebrae. The connecting member, individual lateral spacers, or the entire spinal spacer can be made of bone in order to promote fusion of the vertebrae. The modular construction permits use of bone segments otherwise unsuitable due to size or strength in stable fusion devices.

39 Claims, 12 Drawing Sheets

MODULAR INTERBODY FUSION IMPLANT

FIELD OF THE INVENTION

The present invention relates to implants for use in interbody fusion and methods of manufacturing such implants. More specifically, the present invention relates to implants formed from bone that are useful to restore height and promote bone fusion after a discectomy and methods for manufacturing such implants.

BACKGROUND OF THE INVENTION

One of the leading causes of lower back pain and disability results from the rupture or degeneration of one or more lumbar discs in the spine. Pain and instability are caused by compression of spinal nerve roots by protruding damaged discs into the vertebral canal. Further, the damaged discs do not provide sufficient biomechanical support to allow a full range of vertebral motion. Normally intervertebral discs, which are located between end plates of adjacent vertebrae, stabilize the spine and distribute forces between the vertebrae and cushion vertebral bodies. These intervertebral discs include a semi-gelatinous component (nuclear pulpous), and a stiff fibrous ring (annulus fibrosis). The spinal discs may be displaced or damaged due to trauma, disease, or aging. A herniated or ruptured annulus fibrosis may result in nerve damage, pain, numbness, muscle weakness, and even paralysis. Furthermore, as a result of the normal aging process, discs may dehydrate and harden. This hardening of the disc reduces the disc space height which in turn produces instability of the spine and decreased mobility.

In the more severe cases, the disc tissue is irreparably damaged, and the entire disc has to be removed (discectomy). The discectomy is often followed by a fusion of adjacent vertebrae in order to stabilize the spine. In order to alleviate pain, abnormal joint mechanics, premature development of arthritis, and nerve damage, the disc space between the adjacent vertebrae may be maintained following the discectomy. Spacers or implants are used to maintain the intervertebral space between the adjacent vertebrae.

Current treatment methods utilize grafts of either bone or artificial implants to fill the intervertebral space between adjacent vertebrae. It is desirable that these implants not only fill the disc space vacated by the damaged disc, but also restore the disc space height to pre-damaged conditions. An implant must be sufficiently strong to bear substantially all of the body's weight above the intervertebral space. Furthermore, it is desirable to use the implants to promote fusion of adjacent vertebrae across the disc space and thereby promote mechanical stability. To be successful the implant must provide temporary structured support and allow bone growth to establish fusion between the adjacent vertebrae. Success of the discectomy and bony fusion typically requires the development of a contiguous growth of bone between adjacent vertebrae to create a solid mass of bone capable of withstanding the cyclic compressive spinal loads for the life of a patient.

Current methodologies use implants or grafts made of metal, plastic composites, ceramics, or bone. Natural bone grafts may be developed from autograft, allograft or xenograft. Other bone grafts may include certain man-made substances including binder joining bone chips, composite bone structures, ceramics minimizing bone, etc. The use of bone implants offers several advantages over the use of artificial spacers or implants. The bone implants have a suitable modulus of elasticity that is comparable to that of adjacent vertebrae. The bone implants can be provided with voids that can be packed with cancellous bone or other osteogenic material to promote bone growth and fusion between adjacent vertebrae. Implants formed by cortical bone have sufficient compressive strength to provide a biomechanically sound intervertebral spacer. Further, the implant bone will be replaced over time with the patient's own bone through the process of creeping substitution. In contrast to the bone implants, artificial implants do not fully incorporated into the fusion mass.

As more fully described in U.S. Pat. No. 5,397,364 to Kozak et al., incorporated by reference herein in its entirety, one principle in implant design is that the load transmitted between adjacent vertebrae should be on the strongest part of the vertebral body. This patent describes the desirability of concentrating the heaviest loads on or near the ring apophysis to avoid subsidence of the device into the surrounding vertebral end plates and subsequent collapse of the intradiscal space.

Another principle in implant design is that a spacer should be structured such that implantation of the spacer is minimally invasive. Relatively large single piece spacers capable of transmitting loads to the ring apophysis require large incisions in order to be implanted between vertebrae. Such incisions extending the full width of the disc space create potential problems. More specifically, blood vessels, nerves, ligaments, muscles and other tissue naturally occurring adjacent the effected disc space must be severed or retracted out of harms way. In some cases, such as blood vessels and nerves, the obstructing structure may not be moved without permanent damage to the patient. In these cases, large implants may not be used.

In addition to the damage done to the tissues surrounding the disc space and the extended healing time required to recover from the trauma, damage done to the ligaments extending between adjacent vertebrae may negatively impact the success of the operation. The severed or stretched ligaments may no longer function to maintain tension on the disc space thereby allowing the implant to migrate. Further, unexpected movement between the vertebra and the implant may prevent or impede bone fusion.

A further consideration is that a spacer fit the patient's intradiscal anatomy in order to restore the proper anatomic relationship between the disc, pedicle, nerve root, and facet joints. Restoration of normal disc height will also return the disc annulus to tension, reduce annular bulge and promote stability. At the same time, the device should not shield the spine from all of the stresses normally borne by the spine, since it has been found that reduction of normal stress on the vertebrae can result in bone loss. Also, a spacer should be able to be slowly incorporated into the patient's own body in order to create a stronger fusion mass between vertebrae.

The availability of suitable bone is another consideration when developing bone grafts for disc space insertion. As will be appreciated, only certain bones in the human body have sufficient cortical bone mass to support the loads commonly experienced in the spine. While the potential exists for greater availability of suitable bone sources from animals, at present, such sources are not commercially viable due, at least in part, to the potential for rejection by the human body. A further factor is the relatively few people who agree to donor their bodies for these uses. Thus, there is a need to develop superior implants for interbody fusion from the imperfect donor bone stock available.

With these goals in mind, the Applicants have developed a spinal spacer and method of manufacturing according to the present invention.

SUMMARY OF THE INVENTION

The present invention is directed to an interbody fusion device for engagement between vertebrae. The fusion device includes a pair of lateral spacers for spacing the vertebrae and a connecting member made of bone which is adapted to couple together the lateral spacers when the spacer is inserted between the vertebrae.

The present invention is also directed to a modular interbody fusion device that includes a first bone element, a second bone element, and a third bone element. The first, second, and third bone elements are adapted for coupling together when inserted between vertebrae.

In addition, the present invention is directed to a spinal spacer that includes a pair of lateral spacers made of bone and a connecting member which is adapted to couple the lateral spacers together when inserted between vertebrae. In a preferred embodiment, the lateral spacers include channels for receiving a portion of the connecting member.

The present invention is also directed to a method of manufacturing a spinal spacer. The method of manufacturing the spinal spacer includes obtaining a first piece of bone having a first medial side with a portion thereof defined by a first medullary canal portion. Further, the method includes obtaining a second piece of bone having a second medial side with a portion thereof defined by a second medullary canal portion, and obtaining a third piece of bone with a medullary canal defined therein. The method also includes forming a first structure in the first medial side of the first piece of bone, forming a second structure in the second medial side of the second piece of bone, and forming a third and fourth structure in the third piece of bone configured for engagement with the first and second structures, respectively.

In still another aspect of the present invention, a method for implanting bone grafts for spinal fusion is provided. The method includes positioning a first bone graft in a first lateral portion of the disc space and positioning a second bone graft in a second lateral portion of the disc space opposite said first lateral portion. The method further includes positioning a central spacer between said first and second bone grafts. Preferably, said spacer interconnects the first and second bone grafts. Still more preferably, the first and second bone grafts include grooves and the central spacer includes corresponding rails. In this embodiment, the inserting step also includes aligning the rails within the grooves before insertion.

Further objects, features, benefits, aspects, and advantages of the present invention shall become apparent from the detailed drawings and descriptions provided herein.

DESCRIPTION OF THE PREFERRED EMBODIMENTS

For the purposes of promoting an understanding of the principles of the present invention, reference will now be made to the embodiments illustrated in the drawings, and specific language will be used to describe the same. It will nevertheless be understood that no limitation of the scope of the invention is intended thereby. Any alterations and further modification in the described processes, systems, or devices, and any further applications of the principles of the invention as described herein are contemplated as would normally occur to one skilled in the art to which the invention relates. Preferred embodiments of the invention are shown in great detail, although it will be apparent to those skilled in the relevant art that some of the features may not be shown for the sake of clarity.

Figure 1:
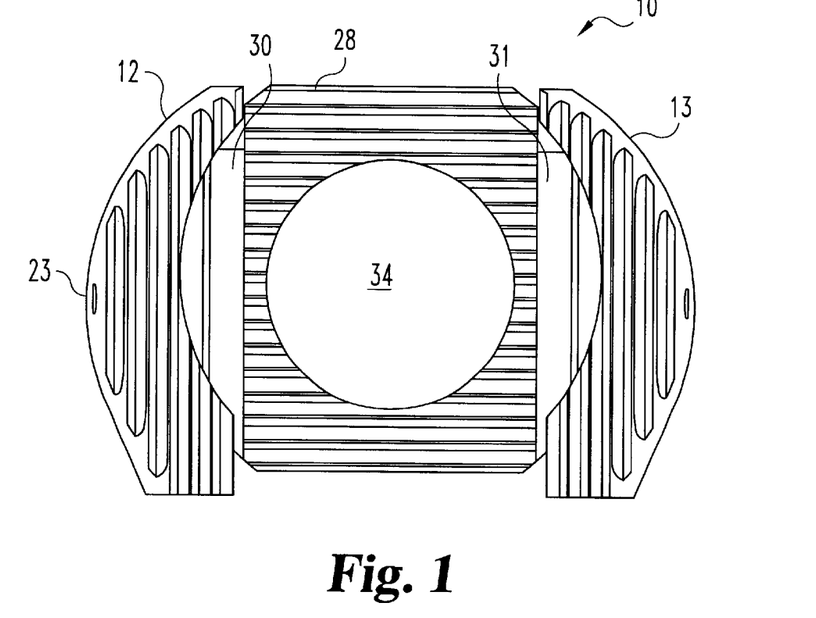
FIG. 1 is a top-view of a spinal spacer according to a first embodiment of the present invention.
Figure 2:
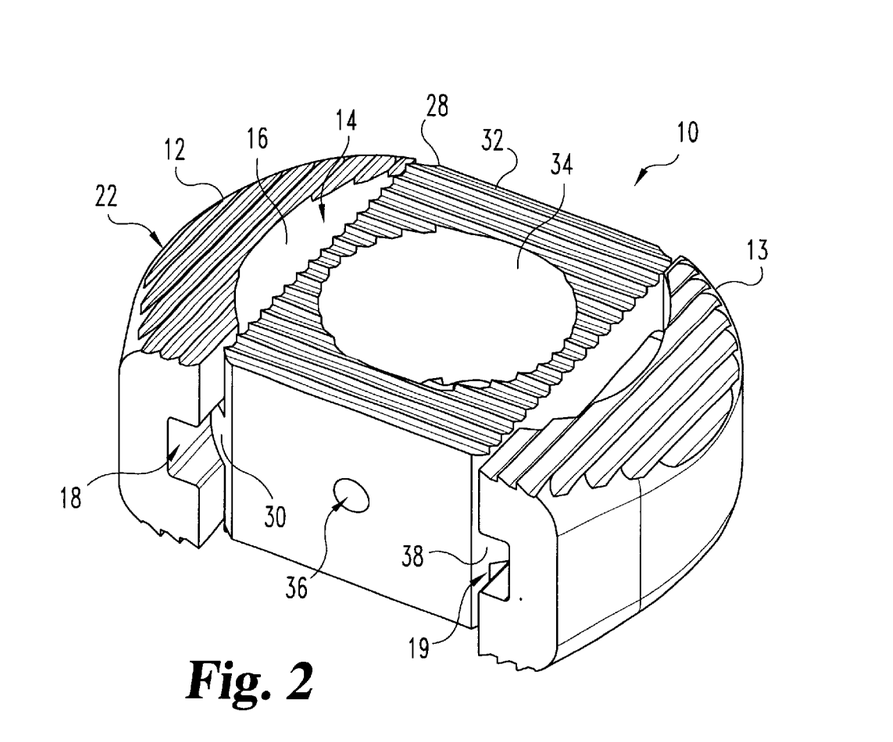
FIG. 2 is a perspective view of the spinal spacer of FIG. 1.

Referring now to FIGS. 1–2, a spinal spacer 10 according to a first preferred embodiment of the present invention is shown. The spinal spacer 10 includes a pair of lateral spacers 12 and 13, and a connecting member 28 engaged between the two lateral spacers. In a preferred aspect the connecting member 28 makes the spinal spacer 10 a substantially rigid structure that inhibits movement of the lateral spacers once inserted between vertebrae.

Figure 3A:
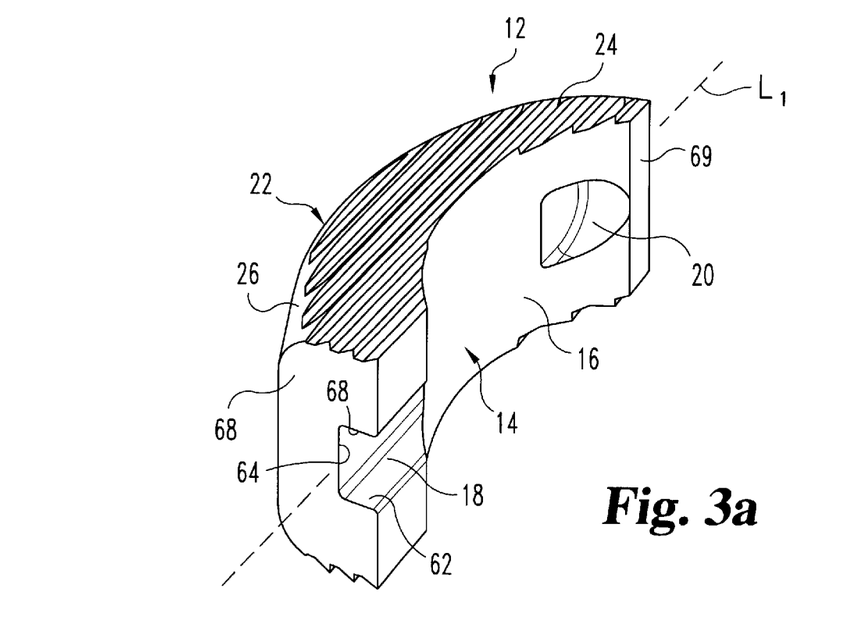
FIG. 3a is a perspective view of a lateral spacer.
Figure 3B:
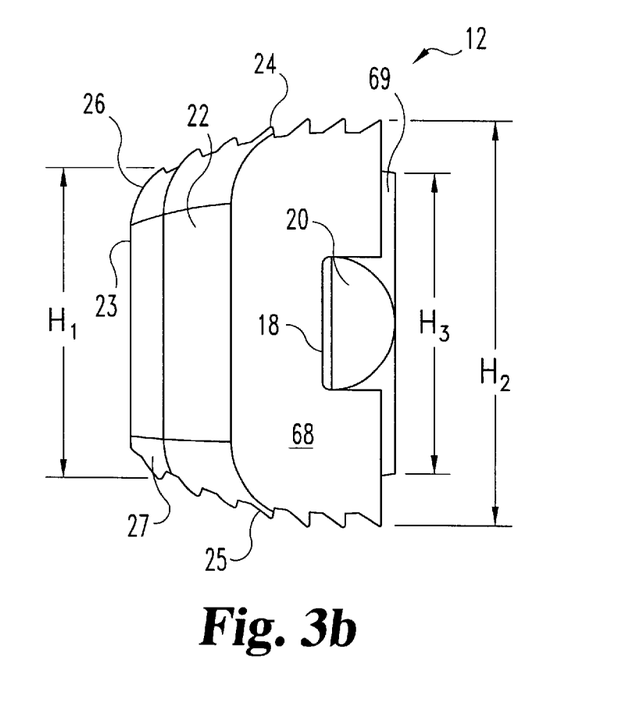
FIG. 3b is an end view of the lateral spacer.

Referring to FIGS. 1–2, it will be appreciated that in a preferred embodiment lateral spacers 12 and 13 are substantially identical mirror images of each other. Thus, the following detailed description of lateral spacer 12 applies equally to lateral spacer 13. As shown in FIGS. 3a–3b, the lateral spacer 12 has a medial side 14 adapted for coupling to the connecting member 28. Further, the lateral spacer 12 has a lateral side 22 which is opposite from the medial side 14. The term "lateral" refers to the lateral portion of the spine and the term "medial" refers to the medial portion of the spine. Spacer 12 includes an upper vertebra engaging surface 24 and a lower vertebra engaging surface 25. Preferably, the upper and lower surfaces 24 and 25 include ridges, such as shown in the figures, or other anti-migration structures defined on the surface to limit movement of the device in the disc space. It is contemplated that the grooves can be oriented and configured in a different manner in order to prevent migration in various directions. Beveled edges 26 and 27 extend between the lateral side wall 22 and the upper and lower surfaces 24 and 25, respectively. These beveled edges 26 which make insertion of the spinal spacer 10 easier between adjacent vertebrae. Further, these beveled edges 26 reduce the trauma to surrounding tissue that might be caused by a spacer that has sharp edges. The lateral side 22, as shown in FIGS. 3a–3b, has an arcuate shape in order to generally coincide with the relatively strong ring apophysis of the vertebral body (see B3 of FIG. 9).

In addition to the convex lateral wall 22 adapted to conform to the vertebral endplate geometry, in a preferred aspect, the height of lateral spacer 12 also approximates the natural geometry of the vertebral endplates. More specifically, the lateral most height $H_1$ of the spacer occurs at the maximum point of curvature 23 of the convex lateral side wall. From this point, the implant increases in height to the maximum height $H_2$ adjacent the juncture of medial side wall 14 and end wall 68. In a preferred aspect of the invention, the transition in height between $H_1$ and $H_2$ is gradual and substantially continuous. Still more preferably, the upper and lower surfaces 24 and 25 curve in a non-linear fashion between the height $H_1$ on the lateral side to the height $H_2$ on the medial side to form a convex surface. [Is there a known radius of curvature?] Still further, for some applications it may be desirable to reduce the implant height from a maximum $H_2$ at anterior end 68 to a smaller height $H_3$ at posterior end 69 (see FIG. 14).

Now referring to FIG. 2, the lateral spacer 12 is coupled at its medial side 14 to the connecting member 28. It is contemplated that the lateral spacer 12 can be coupled to the connecting member 28 by using a number of different coupling mechanisms including adhesives, screws, rail/channel connections, bioresorbable fasteners and other mechanisms used to connect components as known to those skilled in the relevant art. As shown in FIG. 2, the lateral spacer 12 according to the first embodiment of the present invention has a channel 18 that couples to rails 30 of the connecting member 28. The channel 18, as shown in FIG. 3a, is formed on the medial side 14 of the lateral spacer 12. In a preferred embodiment, channel 18 extends in substantially parallel alignment to longitudinal axis $L_1$. Channel 18 is defined by lower surface 62, opposing upper surface 66 and intervening side surface 64. The surfaces 62, 64 and 66 are interrupted by concave medial surface 14 and resume adjacent posterior end 69. Preferable channel 18 terminates in an angular end face 20 which acts as a stopper for the rails of the central spacer. The angular shape of end face 20 improves the interconnection between the lateral spacer 12 and the rail 30. If desired, the channel 18 can have a dovetail cross-sectional profile in order to improve the interlock between the channel 18 and the rail 30.

According to a preferred form of the present invention, the lateral spacers 12 are made from bone. If the lateral spacers 12 are made from bone, the lateral spacers 12 can be slowly incorporated into the patient's body after implantation. This in turn will create a stronger fusion mass between the vertebrae. Furthermore, postoperative imaging is better when the lateral spacers 12 are made from bone, because bone does not cause scattering like with metallic implants in CT or MRI imaging.

Figure 3C:
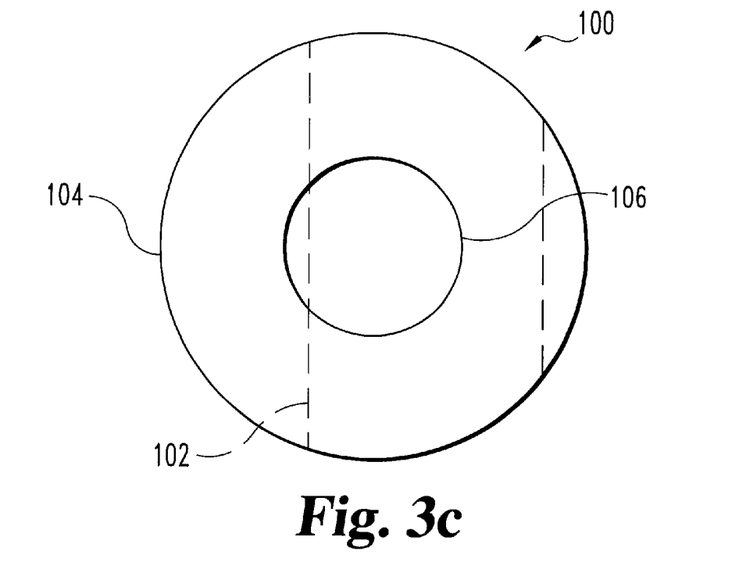
FIG. 3c is a top view of a donor bone.
Figure 3D:
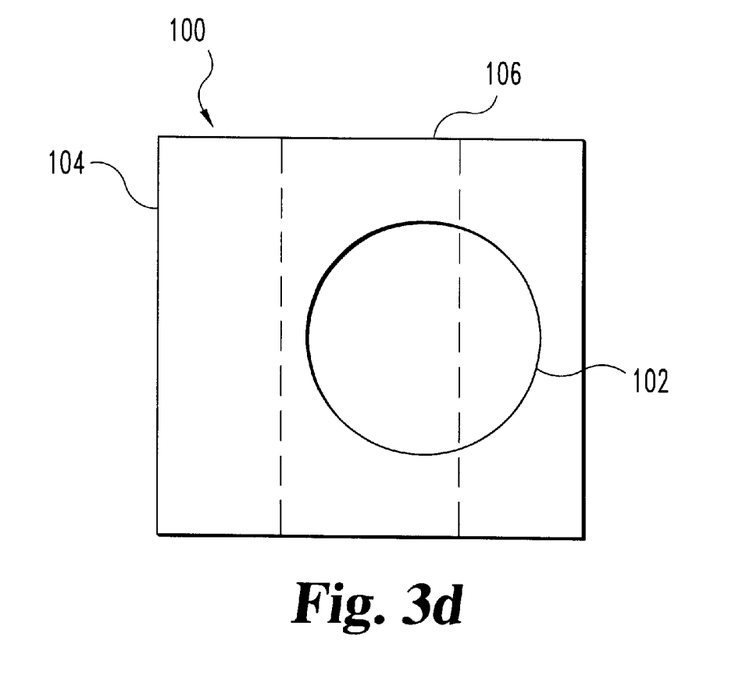
FIG. 3d is a side view of a donor bone.

Lateral spacer 12 may be manufactured using available forms of cortical autograft, allograft or xenograft bone. Multiple lateral spacers 12 may be made from a single bone or from different bones. The lateral spacer 12 may be fabricated from portions of long bone. Since bone for implants is a scarce commodity, it is desirable to use as much of the donor bone as possible. Thus, it is desirable to have the lateral spacer 12 made from remnants of bone. As shown in FIGS. 3c–3d, the lateral spacer 12 may be obtained from remnants of donor bone utilized to form other types of spinal spacers, and from upper and lower end portions of the diaphysis of long bones lacking the required properties. By way of example, a cylindrical bone graft 102 may be cut from donor bone 100. Cylindrical implant 102 takes a portion of the medullary canal 106 but leaves a portion in remnant 104. The remaining bone remnant 104, while too small to be utilized as cylindrical implant, may be formed into an implant suitable for the present invention.

In a preferred embodiment, a portion or the entire medial side 14 of the lateral spacer 12 can be defined by a medullary canal 16 in order to provide a curved surface. As shown in FIG. 3, a portion of the medial side 14 of the lateral spacer 12 can contain a portion of the medullary canal 16. Donor bone can be used more efficiently when the medullary canal 16 is used to define a portion of the medial side. It will be understood that cleaning and preparation of the bone may slightly alter the naturally occurring medullary canal without deviating from the present invention.

Figure 4:
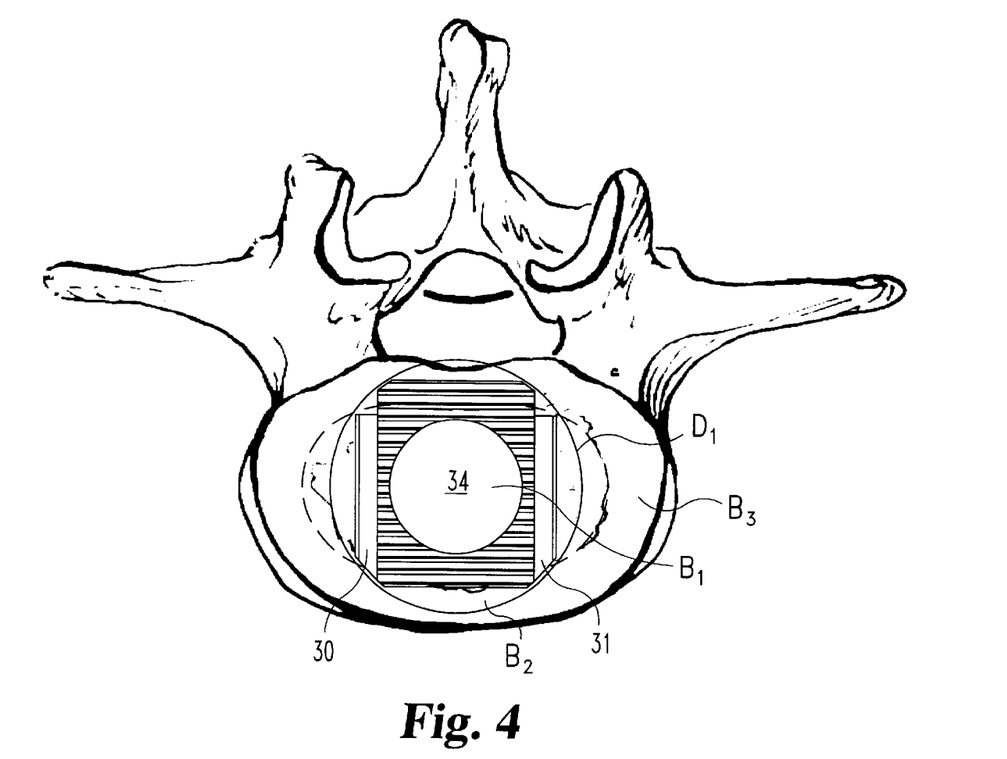
FIG. 4 is a top view of a connecting member according to FIG. 1.

Referring now to FIGS. 1–2, a perspective view of the spinal spacer 10 according to the first embodiment of the present invention is shown. As shown in FIGS. 2 and 4c, the connecting member 28 includes rails 30 and 31, opposing vertebrae engaging surfaces 32 (the identical bottom surface is not shown), central opening 34, guide bore 36, and beveled edges 38. As discussed above, a number of different coupling mechanisms can be used to couple the lateral spacers 12 to the connecting member 28. In the preferred form the rails 30 and 31 are used to couple the connecting member 28 to the lateral spacers 12 and 13. When the connecting member 28 is implanted, the vertebrae engaging surfaces 32 contact corresponding adjacent vertebrae. In addition, these vertebrae engaging surfaces 32 may be grooved in order to reduce migration or expulsion of the inserted spinal spacer 10. In a preferred form, the connecting member 28 includes at least one guide bore 36. Medical instruments can be attached to the connecting member 28 at the guide bore 36 during implantation.

In a preferred form, the connecting member 28 may be manufactured using available forms of autograft, allograft or xenograft donor bone. The donor bone can include cortical bone, cancellous bone, and any combination thereof. After the donor bone is obtained, the bone then can be sculpted according to the size of the intervertebral space. Further, the connecting member 28 may include a medullary canal that naturally defines central opening 34 when the connecting member 28 is formed from bone. As shown in FIG. 4, in a preferred aspect of the invention, donor bone otherwise unsuitable for implantation may be used to form a modular bone graft according to the present invention. More specifically, and by way of example only, a donor bone segment 200 lacks sufficient diameter $D_1$ to provide good contact with the stronger bone of the vertebral endplate, particularly along the lateral edges adjacent the ring apophysis $B_3$. While it may be possible to obtain bone having a sufficient diameter, bone resources are scarce thereby limiting the availability of such bone. Even if available, large sections of the anterior and posterior donor bone portions would be wasted in the machining process to achieve a properly dimensioned spacer. In the preferred embodiment of FIG. 4, the medullary canal extends through the connecting member 28, with openings at both vertebrae engaging surfaces 32. During implantation, the central opening 34 can be filled with bone graft material in order to promote fusion of the vertebrae. The graft material can include cancellous bone, bone chips, or other suitable bone graft substitute material as known in the relevant art. Guide bore 36 may be used to engage an insertion tool (not shown). Further, guide bore 36 may also be used as an injection port so that the graft material can be injected into the central opening 34 after implantation.

In spinal spacer 10 according to the present invention, at least the connecting member 28 or one of the lateral spacers 12 is made from bone in order to promote the creation of a strong fusion mass between the vertebrae after implantation. In a preferred form all three components/elements 12, 28 of the spinal spacer are made from bone (bone elements) and cooperate to form a modular bone graft adapted for interbody fusion.

Figure 5:
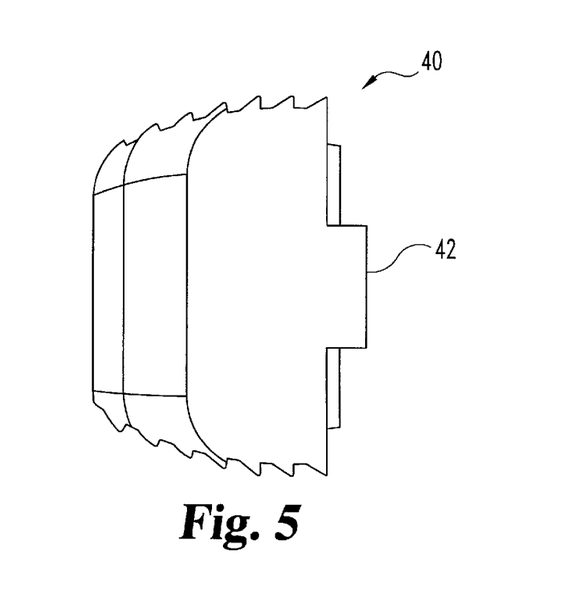
FIG. 5 is an end view of a lateral spacer according to a second embodiment of the present invention.
Figure 6:
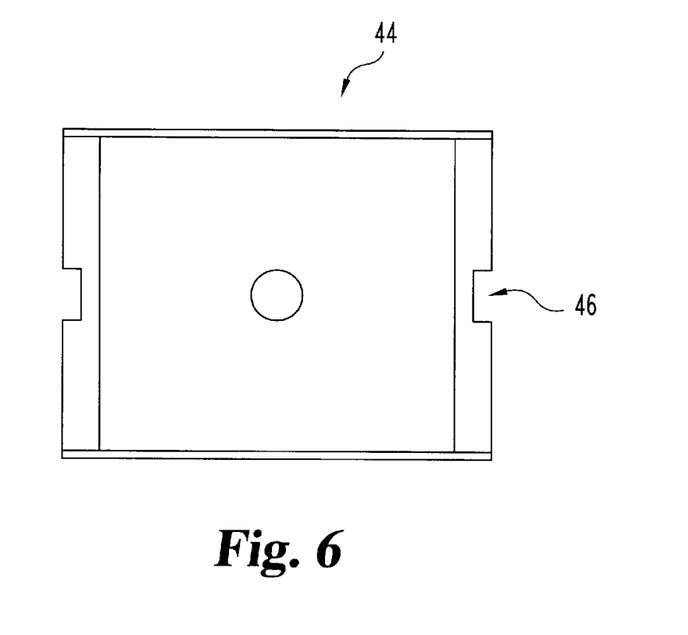
FIG. 6 is an end view of a connecting member according to the second embodiment of the present invention.

A second embodiment of the present invention is shown in FIGS. 5–6. As shown in FIG. 5, a lateral spacer 40 has a rail 42 and not a channel. Accordingly, as shown in FIG. 6, a connecting member 44 has a pair of channels 46 instead of a pair of rails. The lateral spacer 40 and the connecting member 44 then can be coupled together by the rails 42 and channels 46.

Figure 7:
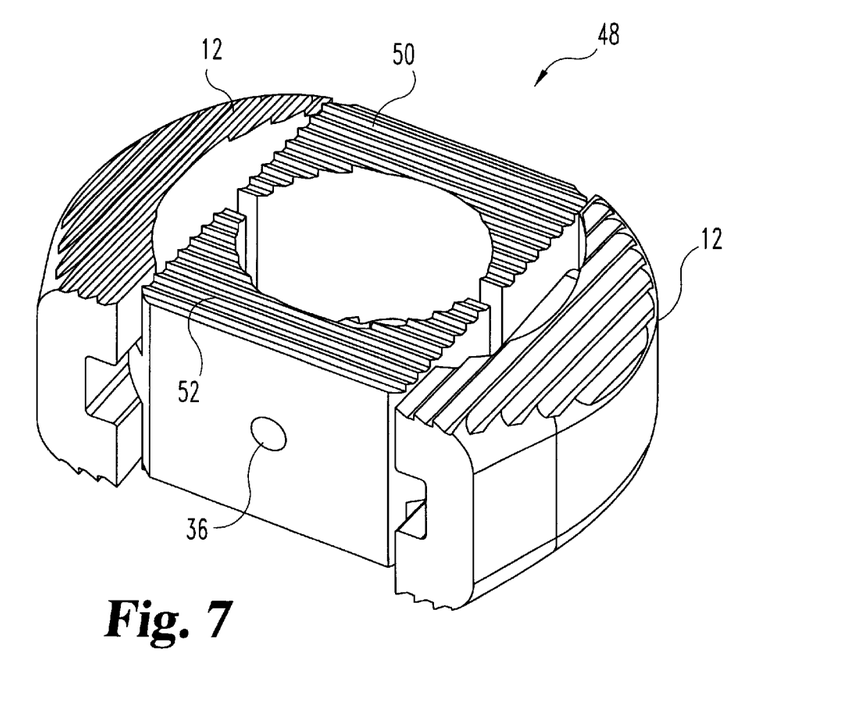
FIG. 7 is a perspective view of a spinal spacer according to a third embodiment of the present invention.

A third embodiment of the present invention is shown in FIG. 7. A spinal spacer 48 according to the third embodiment of the present invention includes a pair of the lateral spacers 12, a first connecting member 50, and a second connecting member 52. The first and second connecting members 50, 52 are coupled to the lateral spacers 12 using the same connecting mechanisms as discussed above. Using the two smaller connecting members 50, 52 instead of a single larger connecting member 28 further reduces the required size of the original bone stock, thereby making more donor bone segments suitable for use in a modular bone graft for spinal fusion.

As explained more fully in U.S. Pat. No. 5,397,364 to Kozak et al., incorporated herein by reference, single piece spinal spacers are not readily adapted for modem anterior fusion techniques. In the early history of anterior fusion, a 15-inch incision was made through the abdomen and a relatively large single piece fusion component was implanted through the incision. More recently, anterior fusion is accomplished through a much smaller 1.5–2 inch incision and does not require splitting of abdominal muscles. In a typical procedure, the surgeon will make an incision of the above-mentioned size in order to permit visualization of approximately 45° of the disc annulus. Newer disc resection techniques are readily adapted to incisions of this limited size. Since the spinal spacer 10 is not a unitary piece, its components 12, 13 and 28 can be easily inserted through a relatively small incision and assembled between the vertebrae.

Furthermore, the spinal spacer 10 when assembled provides a large load-bearing surface which covers a significant portion of the vertebral body. The central portion of a vertebral body contains relatively weak cancellous bone, and the outer portion (apophyseal ring) of the vertebral body contains relatively strong and dense apophyseal bone. When the spinal spacer 10 is assembled, the lateral spacers 12 are positioned over the relatively stronger apophyseal ring of the vertebral body. This configuration allows the vertebrae to be laterally supported at their strongest areas, and subsidence of the spacer 10 into the vertebrae is prevented. Further, the assembled spinal spacer 10 may be tapered in order to better match the intervertebral space.

Figure 9:
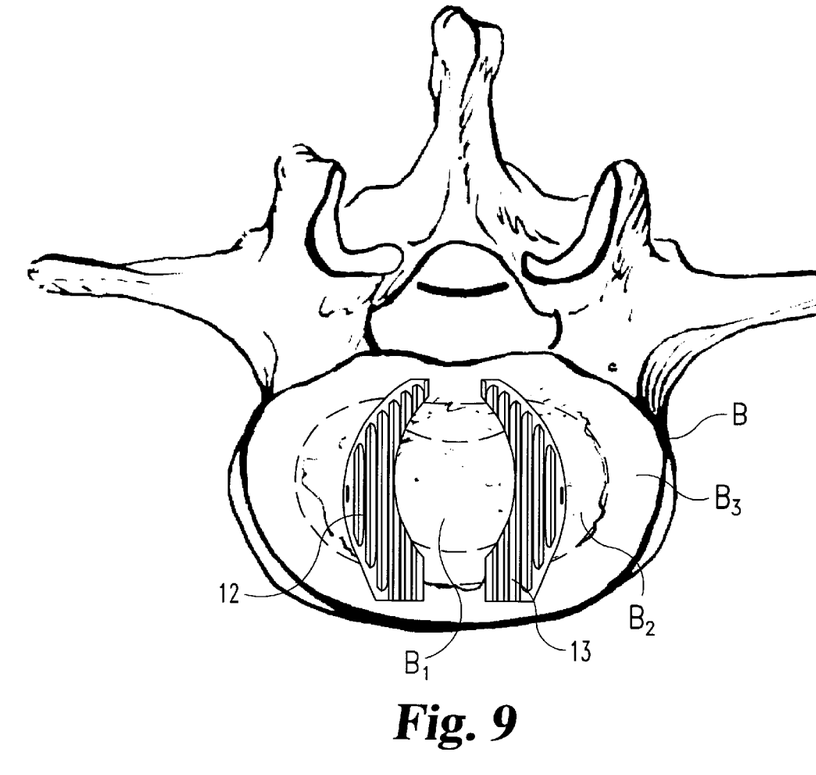
FIG. 9 is a cut-away top view of the lateral spacers of FIG. 8.
Figure 13:
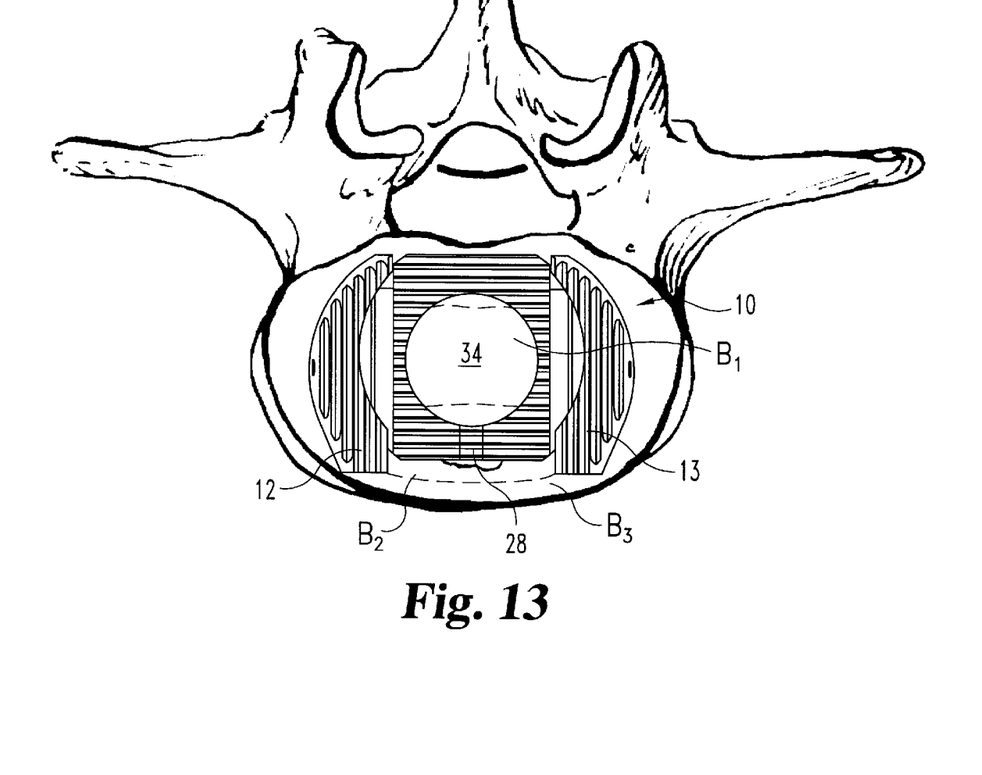
FIG. 13 is a cut-away top view of the spinal spacer of FIG. 12.

A comparison between FIGS. 9 and 13 can illustrate one important feature of the present invention. In FIG. 9, the vertebral body B is represented by its regions of bone strength. The central kidney-shaped portion $B_1$ of the vertebral body B, shown best in FIG. 11, comprises mostly the weak cancellous bone. An annular kidney-shaped region $B_2$ around the central portion contains stronger bone, while the ring apophysis $B_3$ has the strongest bone of the vertebral body. With this in mind, the present invention strives to load those regions of the vertebral body B that have the strongest load-bearing capability. For example, the entire fusion device 10 assumes a generally annular kidney-shape, corresponding to the annular kidney-shape of the stronger bone $B_2$ and $B_3$ in the vertebral body B. This overall shape of the device 10 is achieved by the lateral spacers having each a partial lens shape, while the central spacer 28 has anterior and posterior portions configured to engage the stronger bone regions and the central opening 34 configured to be positioned adjacent weaker bone $B_1$. The bone graft material placed in opening 34 is generally positioned over the weakest portion $B_1$ of the vertebral body B. However, this portion $B_1$ is also known to be highly vascular and biologically active, so that it is an excellent location for bone graft incorporation and fusion.

Figure 8:
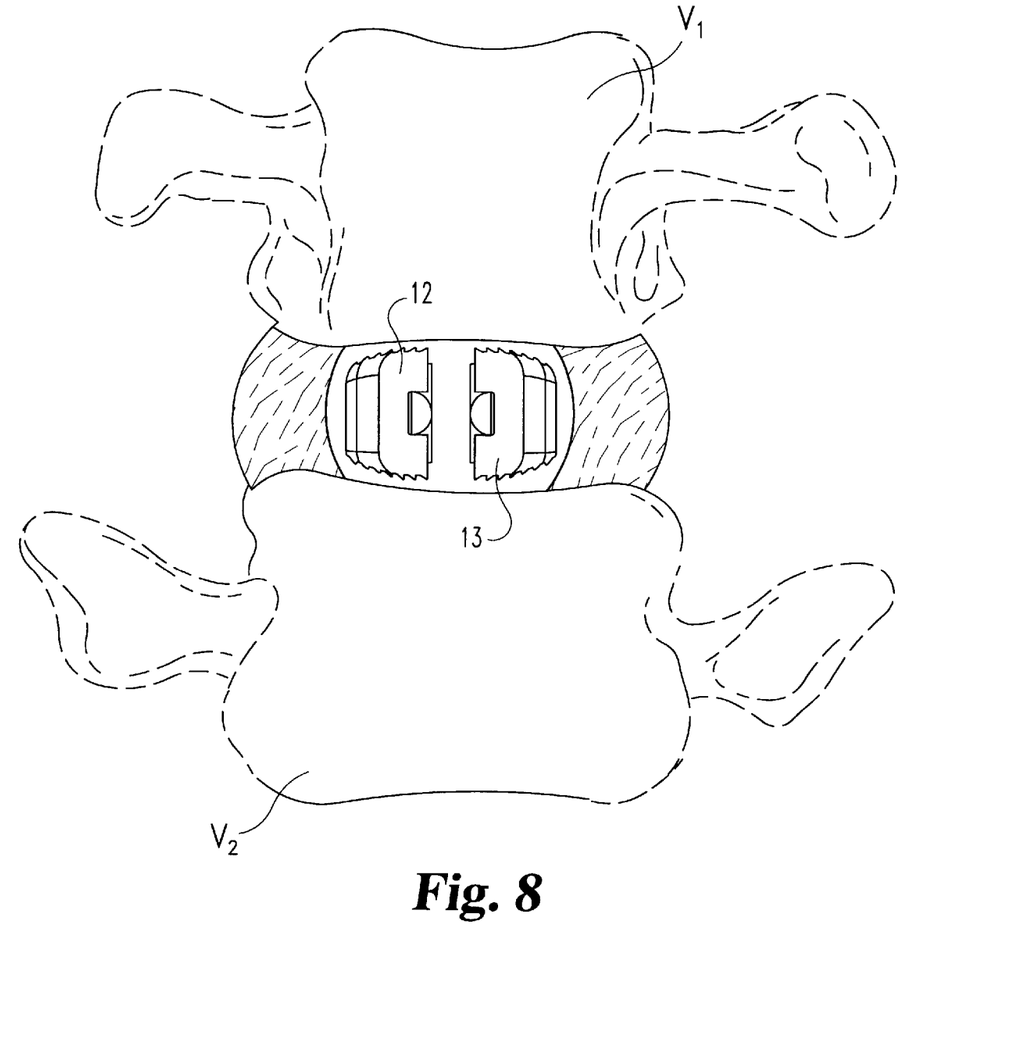
FIG. 8 is an end view of the lateral spacers inserted between vertebrae.
Figure 10:
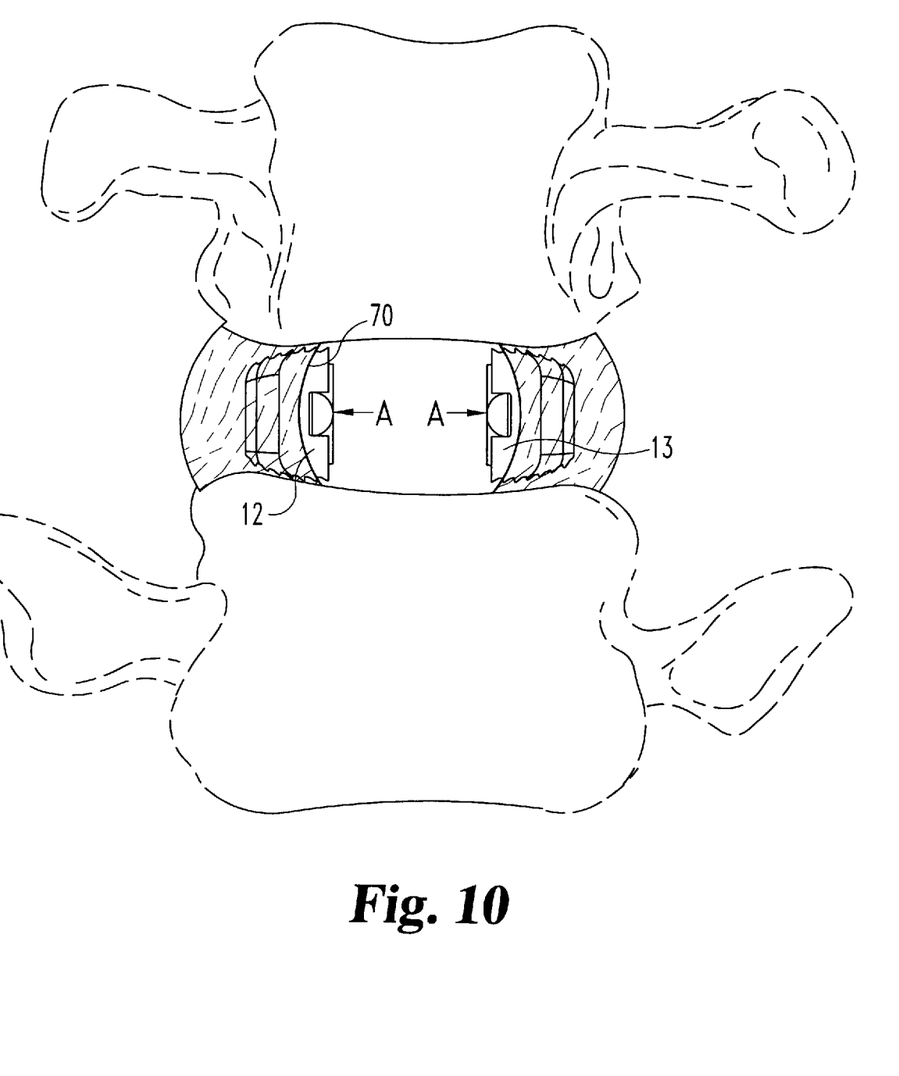
FIG. 10 is an end view of the lateral spacers inserted between the vertebrae.
Figure 11:
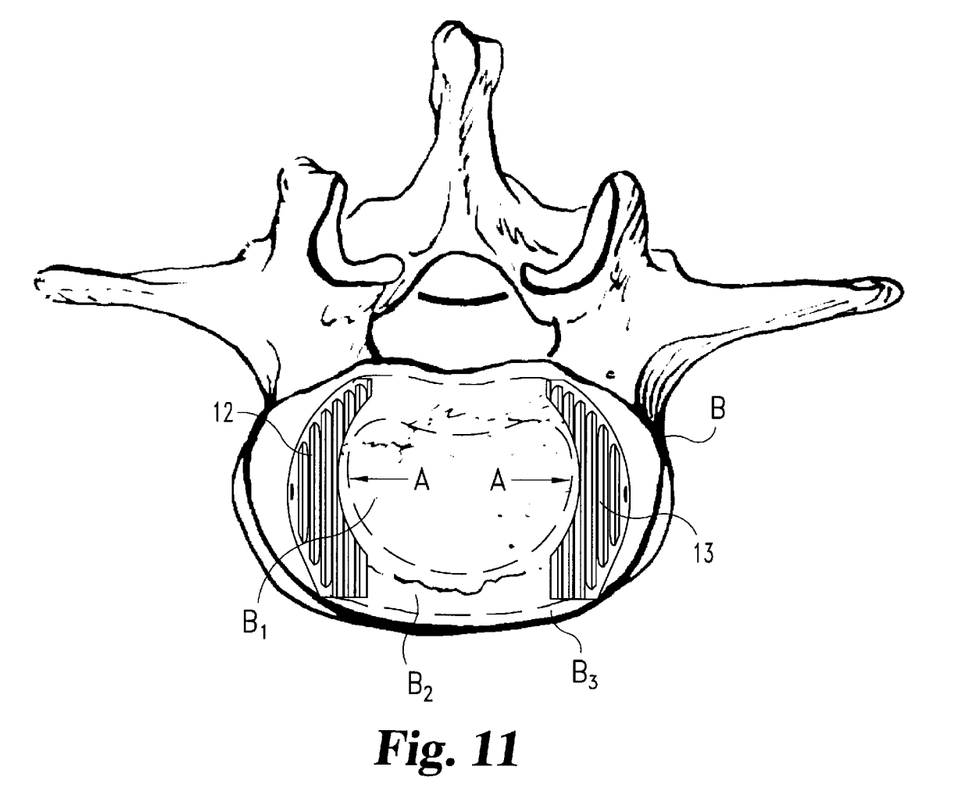
FIG. 11 is a cut-away top view of the lateral spacers of FIG. 10.

FIGS. 8–14 show how the spinal spacer 10, according to a preferred aspect of the present invention, is implanted between adjacent vertebrae. As shown in FIGS. 8 and 9, in one method the lateral spacers 12 and 13 are inserted between the vertebrae from the anterior side. An initial incision, much smaller than the disc space width, is made in the ligaments and other tissue extending between vertebrae $V_1$ and $V_2$. The disc material is removed and the disc space prepared by known surgical techniques which will not be further discussed herein. Lateral spacers 12 and 13 are then inserted through the opening 70 and into the disc space. During initial insertion, the lateral spacers are positioned near the center area of the vertebrae adjacent the much softer bone $B_1$. Referring to FIGS. 10 and 11, the lateral spacers 12 and 13 are then outwardly moved (as shown by arrows A) in order to position the lateral spacers adjacent the lateral portions of the vertebra. Preferably lateral spacers abut bone regions $B_2$ and $B_3$.

Figure 12:
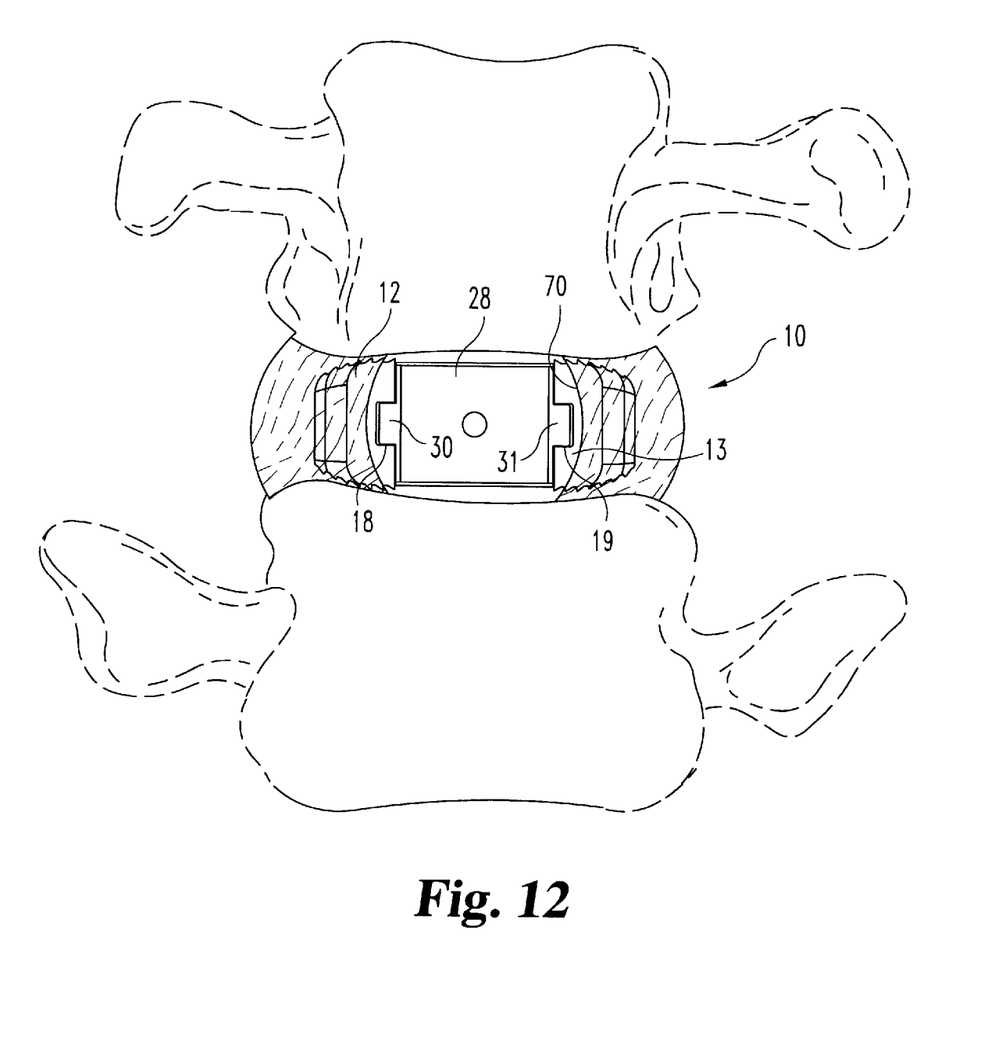
FIG. 12 is an end view of the spinal spacer inserted between the vertebrae.

Referring to FIG. 12, central spacer 28 is positioned adjacent opening 70. Rails 30 and 31 are aligned with corresponding grooves 18 and 19, respectively, in the lateral spacers. The connecting member 12 may be slidably advanced between the lateral spacer 12 to couple the lateral spacers 12 together.

Figure 14:
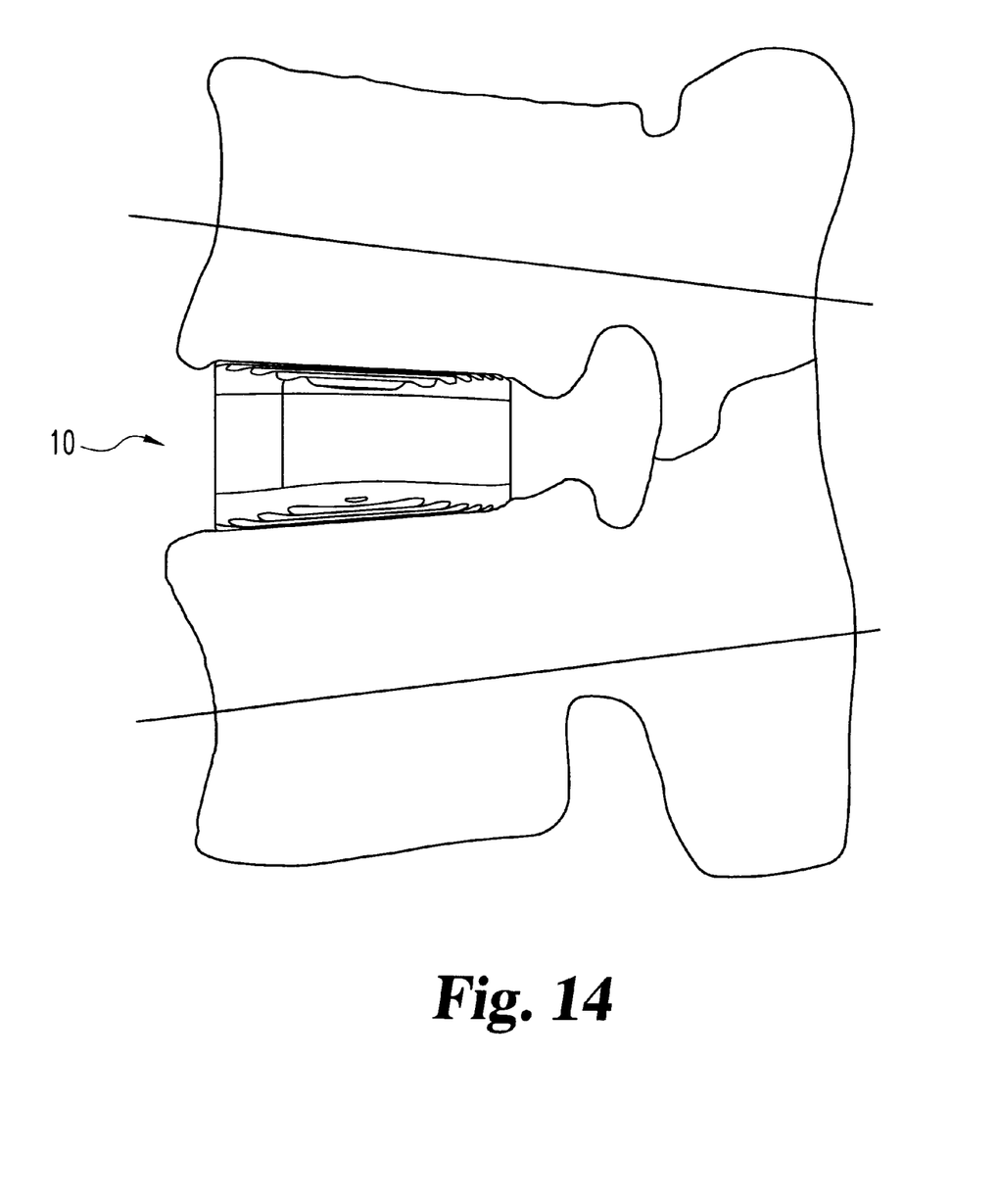
FIG. 14 is a side view of the inserted spinal spacer.

As shown in FIG. 14, the assembled spinal spacer 10 may be configured to match the natural contour of the spine. By way of example, spinal spacer 10 may as shown in FIG. 14 have a wedge-shaped profile or a tapered shape in order to better match the intervertebral space. Further, the lateral spacers 12, according to the present invention, may also have a profile in which the cross-sectional area decreases from the medial side 14 to the lateral side 22 in order to better match the intervertebral space.

While specific embodiments of the invention have been shown and described in detail, the breadth and scope of the present invention should not be limited by the above described exemplary embodiments, but should be defined only in accordance with the following claims and their equivalents. It is understood that only the preferred embodiments have been shown and described and that all changes and modifications that come within the spirit of the invention are desired to be protected.

What is claimed is:

1. A spinal spacer for engagement between vertebrae, comprising:
   a pair of lateral spacers made of bone remnant for spacing the vertebrae, wherein each of said lateral spacers has a medial side, an arcuate lateral side, beveled edges, and a pair of grooved vertebrae engaging surfaces adapted to engage the vertebrae, wherein a portion of said medial side is defined by a medullary canal wall, wherein said medial side has a channel with an angled end face defined therein, and wherein said channel has a dovetail cross-sectional profile; and a connecting member made of bone, wherein said connecting member has a pair of rails engaged with said channels of said lateral spacers, wherein said rails have a dovetail cross-sectional profile, wherein said connecting member has beveled edges, wherein said connecting member has a pair of grooved vertebrae engaging surfaces, wherein said connecting member has a portion of a medullary canal defined therein, wherein said medullary canal has an opening at both of said grooved vertebrae engaging surfaces, and wherein said connecting member has a central guide bore defined therein.

2. A method of manufacturing a spinal spacer, comprising:

obtaining a first piece of bone having a first medial side with a portion thereof defined by a first medullary canal portion, and a first lateral side;

defining a first coupling structure on said first medial side;

obtaining a second piece of bone having a second medial side with a portion thereof defined by a second medullary canal portion, and a second lateral side;

defining a second coupling structure on said second medial side;

obtaining a third piece of bone with at least a portion of a medullary canal defined therein; and defining a pair of rails in the third piece of bone such that the pair of rails are adapted to engage the first and second coupling structures.

3. The method of claim 2, further comprising:

shaping a first pair of grooved vertebrae engaging surfaces on the first piece of bone;

shaping a second pair of grooved vertebrae engaging surfaces on the second piece of bone; and shaping a third pair of grooved vertebrae engaging surfaces on the third piece of bone.

4. The method of claim 3, further comprising: beveling the first lateral side of the first piece of bone; and beveling the second lateral side of the second piece of bone.

5. The method of claim 2, wherein:

the first medial side has a posterior end and an anterior end;

the first medullary canal portion defines a concave surface between the posterior end and the anterior end; and said defining the first coupling structure includes forming a channel that is interrupted by the concave surface between the posterior end and the anterior end.

6. A spinal implant for engagement between vertebrae, comprising:

a pair of lateral spacers formed of bone for spacing the vertebrae, said lateral spacers each having upper and lower vertebrae engaging surfaces adapted to engage the vertebrae, said lateral spacers each having opposite lateral and medial sides disposed between said upper and lower vertebrae engaging surfaces, wherein at least a portion of one of said medial sides is defined by at least a portion of a medullary canal wall; and a connecting member separate constructed and arranged to couple together said lateral spacers at said medial sides when inserted between the vertebrae.

7. The implant of claim 6, wherein said connecting member has a pair of rails, and wherein each of said medial sides of said lateral spacers has a channel defined therein to engage said rails.

8. The implant of claim 7, wherein:

said lateral spacers each has a posterior end and an anterior end; and said anterior end defines an anterior end wall.

9. The implant of claim 8, wherein:

said medullary canal wall defines a concave medial surface; and said channel is interrupted by said concave medial surface and resumes at said posterior end.

10. The implant of claim 9, wherein said channel includes an angular end face at said posterior end to act as a stopper for said rails of said connecting member.

11. The implant of claim 10, wherein said lateral sides each has a convex arcuate shape to coincide with an apophysis ring of the vertebrae.

12. The implant of claim 11, wherein: said lateral spacers have first beveled edges between said lateral sides and said upper vertebrae engaging surfaces; and said lateral spacers have second beveled edges between said lateral sides and said lower vertebrae engaging surfaces.

13. The implant of claim 12, wherein:

said lateral spacers each has a lateral most height at a maximum point of curvature of said convex arcuate shape;

said lateral spacers each has a maximum height at a juncture between said medial sides and said anterior end wall; and said lateral spacers increase in height from said lateral most height to said maximum height.

14. The implant of claim 13, wherein said lateral spacers increase in height in a non-linear fashion from said lateral most height to said maximum height.

15. The implant of claim 14, wherein said connecting member is made of bone with a second medullary canal defining a central opening to receive bone graft material.

16. The implant of claim 15, wherein said central connecting member defines a guide bore adapted to engage an insertion tool, said guide bore being in communication with said central opening to act as an injection port after insertion.

17. The implant of claim 16, further comprising:

a second connecting member made of bone, wherein said second connecting member is adapted to couple together said lateral spacers when inserted between the vertebrae.

18. The implant of claim 17, wherein said upper and lower vertebrae engaging surfaces are grooved.

19. The implant of claim 18, wherein said lateral spacers are made from remnants of bone discarded during fabrication of other implants.

20. The implant of claim 19, wherein said channel has a dovetail cross section.

21. The spinal implant of claim 20, wherein both of said lateral spacers have said medial sides defined by said medullary canal wall.

22. The implant of claim 6, wherein said lateral spacers are made from bone remnants from fabrication of other implants.

23. The spinal implant of claim 6, wherein both of said lateral spacers have said medial sides defined by said medullary canal wall.

24. The implant of claim 23, wherein said connecting member has a pair of rails, and wherein each of said medial sides of said lateral spacers has a channel defined therein to engage said rails.

25. The implant of claim 24, wherein:

said lateral spacers each has a posterior end and an anterior end;

said medullary canal wall defines a concave medial surface; and said channel is interrupted by said concave medial surface and resumes at said posterior end.

26. The implant of claim 25, wherein said channel includes an angular end face at said posterior end to act as a stopper for said rails of said connecting member.

27. The implant of claim 23, wherein:

said medullary canal wall defines concave medial surfaces in said medial sides; and said lateral sides each has a convex arcuate shape to coincide with an apophysis ring of the vertebrae.

28. The implant of claim 6, wherein:

said lateral spacers each has a posterior end and an anterior end;

said medial sides each defines concave medial surface; and said lateral sides each defines a convex arcuate shape to coincide with an apophysis ring of the vertebrae.

29. The implant of claim 28, wherein:

said lateral spacers each has a lateral most height at a maximum point of curvature of said convex arcuate shape;

said lateral spacers each has a maximum height at a juncture between said medial sides and said anterior end wall of each of said lateral spacers; and said lateral spacers increase in height from said lateral most height to said maximum height.

30. The implant of claim 29, wherein said lateral spacers increase in height in a non-linear fashion from said lateral most height to said maximum height.

31. The implant of claim 6, wherein said connecting member is made of bone with a second medullary canal defining a central opening to receive bone graft material.

32. The implant of claim 6, further comprising:

a second connecting member made of bone, wherein said second connecting member is adapted to couple together said lateral spacers when inserted between the vertebrae.

33. The implant of claim 6, wherein said upper and lower vertebrae engaging surfaces are grooved.

34. The implant of claim 6, wherein:

said connecting member defines a pair of channels; and said lateral spacers define rails at said medial sides adapted to engage said channels.

35. The implant of claim 6, further comprising screws to secure said lateral spacers to said connecting member.

36. A spinal implant for engagement between vertebrae, comprising:

a connecting member made of bone remnant with a medullary canal defining a central opening to receive bone graft material; and a pair of lateral spacers each having upper and lower vertebrae engaging surfaces adapted to engage the vertebrae, said lateral spacers each having opposite lateral and medial sides disposed between said upper and lower vertebrae engaging surfaces, wherein said medial sides are adapted to connect to said connecting member, said medial sides each defines concave medial surface, and said lateral sides each defines a convex arcuate shape to coincide with an apophysis ring of the vertebrae.

37. The implant of claim 36, wherein:

said lateral spacers are made of bone remnant; and said concave medial surface of both of said lateral spacers includes at least a portion of a second medullary canal.

38. The implant of claim 36, wherein said connecting member has a pair of rails, and wherein each of said medial sides of said lateral spacers has a channel defined therein to engage said rails.

39. The implant of claim 36, wherein said bone remnant used to make said connecting member lacks sufficient size to contact the apophysis ring of the vertebrae.

\* \* \* \* \*